United States Patent [19]

Trojanowski et al.

[11] Patent Number: 5,601,985
[45] Date of Patent: Feb. 11, 1997

[54] METHOD OF DETECTING ABNORMALLY PHOSPHORYLATED TAU(τ)

[75] Inventors: John Q. Trojanowski; Virginia M-Y. Lee, both of Philadelphia, Pa.

[73] Assignee: Trustees of the Univ. of Pennsylvania, Philadelphia, Pa.

[21] Appl. No.: 495,308

[22] Filed: Jun. 27, 1995

Related U.S. Application Data

[60] Division of Ser. No. 145,827, Oct. 29, 1993, which is a continuation-in-part of Ser. No. 745,384, Aug. 14, 1991, abandoned.

[51] Int. Cl.$^6$ ........................................ G01N 33/53
[52] U.S. Cl. ..................... 435/7.1; 435/7.92; 435/7.95; 436/518
[58] Field of Search ........................ 435/7.1, 7.9, 7.92, 435/7.93, 7.94, 7.95; 436/518

[56] References Cited

PUBLICATIONS

H. C. Chui, *Arch. Neurol.* (Chicago) 46, 806 (1989).
D. L. Price et al., *BioEssays* 10, 69 (1989).
D. J. Selkoe, *Annu. Rev. Neurosci*, 12, 463 (1989).
J. Q. Trojanowski et al, *Annu. Rev. Gerontol. Ceriat.*, 10, 167 (1991).
C. M. Wischik, *Curr. Opin. Cell Biol.* 1, 115 (1989).
S. G. Greenberg and P. Davies, *Proc. Natl. Acad. Sci. U.S.A.* 87, 5827 (1990).
M. Geodert et al., ibid, 85, 4051 (1988).
J. Kondo et al., *Neuron* 1, 827 (1988).
C. M. Wischik et al, *Proc. Natl. Acad. Sci. U.S.A.* 85, 4506, (1988).
B. L. Wolozin et al., *Science* 232, 648 (1986).
B. L. Wolozin et al. *Proc. Natl. Acad. Sci. U.S.A.* 85, 6202 (1988).
H. Ksiezak–Reding et al., *J. Biol. Chem.* 263, 7943 (1988).
N. Nukina et al., *Neurosci. Lett.* 87,240 (1988).
H. Ksiezak–Reding et al., *J. Neurosci, Res.* 25, 420 (1990).
H. Ksiezak–Reding et al., *J. Neurosci Res* 25:412 (1990).
H. Arai, et al., *Proc. Natl. Acad. Sci. U.S.A.* 87, 2249 (1990).
M. L. Schmidt. V.M.-Y. Lee J. Q. Trojanowski, *Am. J. Pathol.* 136, 1069 (1990).
R. A. Stern, L. Otvos. Jr., J. Q. Trojanowski, V.M.-Y. Lee, ibid, 134, 973 (1989).
V.M.-Y. Lee, B. J. Balin, L. Otvos. Jr., J. Q. Trojanowski, unpublished data.
M. Goedert, M. G. Spillantini, M. C. Potier, J. Ulrich, R. A. Crowther, *EMBO J.* 8, 393 (1989).
M. Goedert, M. G. Spillantini, R. Jakes, D. Rutherford, R. A. Crowther, *Neuron* 3, 519 (1989).
R. B. Vallee, *J. Cell Biol.* 92, 435 (1982).
J. Q. Trojanowski, T. Schuck, M. L. Schmidt, V. M.Y–Lee, *J. Histochem. Cytochem.* 37, 209 (1989).
K. S. Kosik et al., *Neuron* 1, 816 (1988).
Grundke–Iqbal et al., *Proc. Natl. Acad. Sci. U.S.A.* 83, 4913 (1986).
V. M.-Y. Lee et al., ibid, 85, 1998 (1988).
V. M.-Y. Lee, L. Otvos, Jr., M. L. Schmidt, J. Q. Trojanowski, ibid, p. 7384.
L. Otvos et al., *Int. J. Pept. Protein Res.* 34, 129 (1989).
Y. Ihara, *Brain Res.* 459, 138 (1988).
N. W. Kowall and K. S. Kosik, *Ann. Neurol.* 22, 639 (1987).
A. C. McKee et al., ibid. 26, 652 (1989).
D. W. Cleveland, *Cell.* 60,701 (1990), G. Lee et al., *Neuron* 2, 1615 (1989).
S. A. Lewis et al., *Nature* 342, 498 (1989).
K. Iqbal et al., *Proc. Natl. Acad. Sci. U.S.A.* 86, 5646, (1989).
T. Miyakawa et al., *Virchows Arch.* B 57, 267 (1989).
G. McKhann et al., *Neurology* 34, 939 (1984).
Z. S. Khachaturian, *Arch. Neurol.* 42, 1097 (1985).
G. Lee et al., *Neuron* 2, 1615 (1989).

*Primary Examiner*—Marian C. Knode
*Assistant Examiner*—Patricia A. Duffy
*Attorney, Agent, or Firm*—Law Offices of Jane Massey Licata

[57] ABSTRACT

Antibodies specifically reactive with an abnormally phosphorylated peptide comprising SEQ ID NO: 3 wherein a serine in SEQ ID NO: 3 is abnormally phosphorylated are provided. Methods of detecting abnormally phosphorylated τ in a test sample and methods of diagnosing Alzheimer's Disease with these antibodies are also provided.

4 Claims, 5 Drawing Sheets

METHOD OF DETECTING ABNORMALLY PHOSPHORYLATED TAU(τ)

This application is a continuation in part of U.S. Ser. No. 08/145,827, filed Oct. 29, 1993, pending, which is a continuation of Ser. No. 07/745,384, filed Aug. 14, 1991, now abandoned.

FIELD OF THE INVENTION

This invention relates to the field of medical diagnostics. More particularly, the invention relates to a method of diagnosing a disease in a person associated with the accumulation of paired helical filaments by identifying the presence of an abnormally phosphorylated serine in the sequence Lys Ser Pro Val (SEQ ID NO: 3) of the protein τ.

BACKGROUND OF THE INVENTION

Alzheimer's Disease (AD) is a disorder of the later decades of life characterized by dementia. In clinical terms, it consists of a diffuse deterioration of mental function, primarily in thought and memory and secondarily in feeling and conduct. Alzheimer's Disease has been used to designate dementia appearing before the age of 65 years. When the syndrome presents after that age, the term senile dementia of the Alzheimer's type is used. In fact, it appears reasonable to consider both types as representing a single syndrome. The true incidence of the disorder is unknown, although recent data suggest that the incidence of all dementia in the U.S. population may be over 100 cases per 100,000, with its prevalence being over 550 per 100,000. Alzheimer's Disease probably affects at least 30 to 50% of patients with dementia, and in the United States there may be over one million individuals with severe dementia and several million more with mild to moderate dementia. It has been estimated that 1 out of every 6 persons over the age of 65 in the United States suffers form moderate dementia, and a majority of patients in nursing home populations are affected with the disorder. The average age of onset is between 70 and 79 years, but without better information on the population at risk, a more accurate statement is not presently possible. The incidence of the syndrome clearly increases with advancing age. A family history of Alzheimer's Disease is present in 5 to 10% of the patients.

At the present time, the clinical diagnosis of Alzheimer's Disease is one of exclusion. Secondary causes of loss of memory and impaired cognitive function may result from multiple infarcts, leading to so-called multi-infarct dementia, or from intracranial mass lesions such as subdural hematomas, brain tumors, or granulomas. Central nervous system infections of viral and bacterial origin, or even slow vital disorders such as Jakob-Creutzfeldt Disease, are part of the differential diagnosis. Furthermore, metabolic disorders involving vitamin $B_{12}$ metabolism, thiamine or folate deficiency, thyroid dysfunction, hepatic and renal failure, as well as drug toxicity may present as dementia. Nevertheless, when all these secondary causes, many of which are reversible, are eliminated, cerebral atrophy of unknown cause or Alzheimer's Disease still covers the largest number of patients. Elevations of aluminum content in brain have been implicated in the pathogenesis of the disorder but appear to be secondary rather than primary.

The pathological picture of Alzheimer's Disease has been well characterized over the years. It consists of senile plaques, which result from degeneration of nerve endings, and neurofibrillary tangles, which represent an alteration in the cytoskeletal apparatus. In addition, intracellular cytoplasmic eosinophilic inclusions, termed Hirano bodies, are present, primarily in the hippocampus. Granulovascular degeneration is also noted. Senile plaques and neurofibrillary tangles in the brain are part of the "normal" aging process. However, at any age, patients with clinical Alzheimer's Disease appear to have a much higher concentration of these abnormalities than do normal individuals.

Paired helical filaments (PHFs) are the principal structural elements of AD neurofibrillary tangles (NFTs) (1). Although not restricted to AD, the number of NFTs correlates with the severity of dementia in AD (1). PHFs also occur in the neurites surrounding amyloid-rich senile plaque (SP) cores, and in neuropil-threads (NTs) that represent altered neuronal processes (1). Low $M_r$ microtubule-associated proteins (MAPs) known as τ are major constituents of PHFs (1). A soluble form of PHFs may be formed from τ (2). Although other neuronal-cytoskeleton polypeptides also may be components of NFTs and the neurites in SP coronas (1), only peptide sequences from the COOH-terminal third of τ have been recovered directly from purified AD PHFs (3). The 60- to 68-kD polypeptides, previously known as A68 and now referred to as PHFτ, were initially identified with the ALZ50 monoclonal antibody (MAb) and were thought to be AD-specific and present in NFTs (4). Despite immunological and biochemical data that imply that A68 is a modified form of τ, this hypothesis is controversial, and the mechanism whereby this modification could occur is unknown (5, 6). For example, almost all available antibodies to τ, including ALZ50, react with A68 (5). Nevertheless, A68 has a higher $M_r$, a more acidic isoelectric point, and far lower solubility in nonionic detergents than τ (7). Hence, the precise relation of A68 to τ and to PHFs is unknown.

Accordingly, there remains a need for rapid and accurate methods of detecting Alzheimer's Disease.

SUMMARY OF THE INVENTION

There is provided by this invention novel substantially purified antibodies and monoclonal antibodies specifically reactive with a peptide comprising the sequence Lys Ser Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated.

There is further provided by the invention a novel method of diagnosing a disease associated with the accumulation of paired helical filaments in a person comprising identifying in a test sample from said person τ which has an abnormally phosphorylated serine in the sequence Lys Ser Pro Val (SEQ ID NO: 3), whereby said identification is diagnostic of a disease associated with the accumulation of paired helical filaments in a person.

There is further provided by the invention a novel test kit for diagnosing a disease associated with the accumulation of paired helical filaments comprising:

(a) antigens capable of binding with antibodies specifically reactive with a peptide comprising the sequence Lys Set Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated; or (b) antibodies specifically reactive with a peptide comprising the sequence Lys Ser Pro Val (SEQ ID NO: 3)

and flanked by amino acids such that said peptide is in the range from 4 to about 40 amino acids in length and characterized in having said Serine in the sequence Lys Ser Pro Val (SEQ ID NO: 3) abnormally phosphorylated.

Putative Alzheimer's Disease (AD)-specific proteins (referred to as A68 or PHFτ) were purified to homogeneity and shown to be major subunits of one form of paired helical filaments (PHFs). The amino acid sequence and immunological data indicate that the backbone of A68 is indistinguishable from that of the protein tau (τ), but A68 could be distinguished from normal human τ by the degree to which A68 was phosphorylated and by the specific residues in A68 that served as phosphate acceptors. The larger apparent relative molecular mass ($M_r$) of A68, compared to normal human τ, was attributed to abnormal phosphorylation of A68 because enzymatic dephosphorylation of A68 reduced its $M_r$ to close to that of normal τ. Moreover, the Lys Ser Pro Val (SEQ ID NO: 3) motif in normal human τ is believed to be an abnormal phosphorylation site in A68 because the Ser in this motif was a phosphate acceptor site in A68, but not in normal human τ. Thus, the major subunits of a class of PHFs are A68 proteins and the excessive or inappropriate phosphorylation of normal τ may change its apparent $M_r$, thus transforming τ into A68.

DETAILED DESCRIPTION OF THE DRAWINGS

Figure 1A:
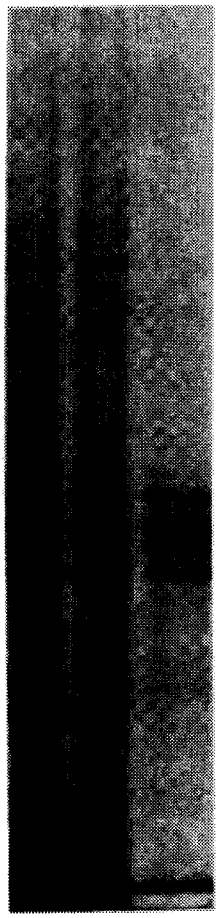
Figure 1B:
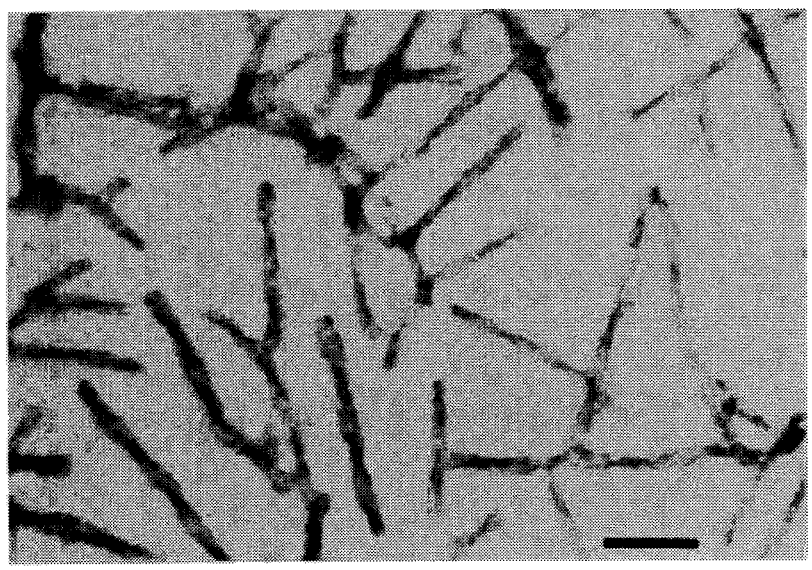
Figure 1C:

FIG. 1(A) shows coomassie brilliant blue-stained gel of A68 and other fractions containing A68 from an AD brain after sarkosyl extraction. The crude A68 preparation was loaded onto a stepwise sucrose gradient and centrifuged in a SW50 rotor at 175,000 g for 16 hours. A thick, dark brown band was recovered at 1.25 to 1.5 M sucrose (fraction 1, lane 1), a thick, light brown band was found at 1.75 to 2.0 M sucrose (fraction 2, land 2), and a small amount of pale brown material was recovered at 2.25 to 2.5 M sucrose (fraction 3, lane 3). Each sucrose fraction was washed once, solubilized in sample buffer, and run on a 7.5% SDS-polyacrylamide gel electrophoresis (SDS-PAGE) gel. Only material in fraction 3 was completely soluble in sample buffer containing SDS where fractions 1 and 2 contained insoluble material after boiling in SDS sample buffer. In lanes 1 and 2, 40 μg of protein was loaded, and in lane 3, 10 μg of protein was loaded so that the amount of A68 would be similar to that in lanes 1 and 2. This was established by quantitative immunoblotting with $^{125}$I-labeled second antibody in parallel experiments. Nevertheless, slight variations from one AD brain to another in the intensity of the A68 proteins stained with Coomassie blue were noted (compare lane 3, FIG. 1A, with lane 4, FIG. 2A). $M_r$ markers (dots to left) were 205,000, 116,000, 77,000 and 46,500 kD. Quantitative immunoblotting showed that fraction 3 contained less than 20% of the total A68 recovered from all three fractions, (9). (FIGS. 1B and 1C show) negatively stained A68 proteins from AD brain preparation like that shown in lane 3 of (A) was placed on Formvar-coated nickel grids, stained with 2% methanolic uranyl acetate, and viewed by electron microscopy. The A68 filaments shown here are identical to classical PHFs, and their diameters fall within the upper range of measurements reported for in situ PHFs, (1, 20). (B) Low magnification (bar=100 nm) views showed abundant PHFs uncontaminated with the amorphous material often associated with NFT and PHF isolates from AD brains (3). (C) At higher magnification (bar=50 nm), the A68-derived PHFs have "fuzzy" margins where these filaments are the widest (30 to 40 nm), but they are smoother along the "twisted" segments where the diameter of the PHFs is constricted (20 nm).

FIGS. 2A to 2F show biochemical and protein immunoblot data for A68, normal human τ, and enzymatically dephosphorylated A68 and normal human τ. (A) Coomassie brilliant blue-stained 10% SDS-PAGE gel. (B through F) Nitrocellulose replicas of gels identical to the one in (A) expect that lane 5 (showing the $M_r$ of E. coli alkaline phosphatase that also is visible in lanes 2 and 3) was omitted in the immunoblots. (A through F): lane 1, human τ; lane 2, enzymatically dephosphorylated human τ (using Type IIIN E. coli alkaline phosphatase from Sigma, St. Louis, Mo.) as described (15); lane 3, A68 dephosphorylated as in lane 2; and lane 4, A68. $M_r$ markers were 116,000, 77,000, 465,000 and 33,000 kD, as indicated to the left of lane 1 in FIG. 2A. The blots in FIGS. 2B, C, and D were probed with three MAbs that bind different τ epitopes (T46, ALZ50, and Tau-1, respectively) (4–6, 10, 12). The gel replicas in (E) and (F) were immunoblotted with the antisera to τ peptides (10 μg/ml anti-T3P and 10 μg/ml anti-T3, respectively), both of which were affinity-purified. The purity of the T3 and T3P peptides, and the location of the phosphate in T3P, were demonstrated by gas-phase microsequencing, fast atom bombardment mass spectrometry, and phosphate analysis. Human τ was purified by cycling the first high-speed brain supernatant in the presence of taxol with exogenous phosphocellulose-purified bovine tubulin (1 mg/ml) (11).

FIGS. 3A to 3F show immunolabeled A68-derived PHFs probed on nickel grids with MAbs to τ or with the antipeptide antibodies. (A) T14, (B) T46, (C) anti-T3P, and (D) anti-T3. A68 was immunolabeled by absorbing purified A68 onto carbon, Formvar-coated grids and blocking for 30 minutes with 2% newborn calf serum plus 1% cold water fish gelatin in Tris-buffered saline. The grids were incubated with primary MAbs (undiluted spent supernatants) or with the peptide-specific antibodies (diluted 1:200:) for 30 minutes. After extensive blocking and washing, the grids were incubated for 1 hour with goat antibody against mouse or rabbit immunoglobulin G conjugated to 5- or 10-nm gold particles, respectively. At the end of the incubation, the grids were washed extensively, negatively stained in 2% methanolic uranyl acetate for 10 minutes, and viewed by electron microscopy. All micrographs are enlarged to the same extent, and the bar in (D)=200 nm. (E and F) Light microscopic immunohistochemical staining patterns produced with anti-T3P (e) and anti-T3 (F) antisera in adjacent 6-μm-thick sections of AD hippocampus. The tissue sections were cut from paraffin-embedded blocks fixed in 70% ethanol with 150 mM NaCl (8). Note the position of the same blood vessel (asterisk) in the center of the field in (E) and (F). The anti-T3P antibody labels NFTs, neurites in SPs, and numerous HTs that are not well visualized at this magnification. The anti-T3 antibody labels only a few NFTs. The magnification in (E) and (F) is X250.

Figure 4:
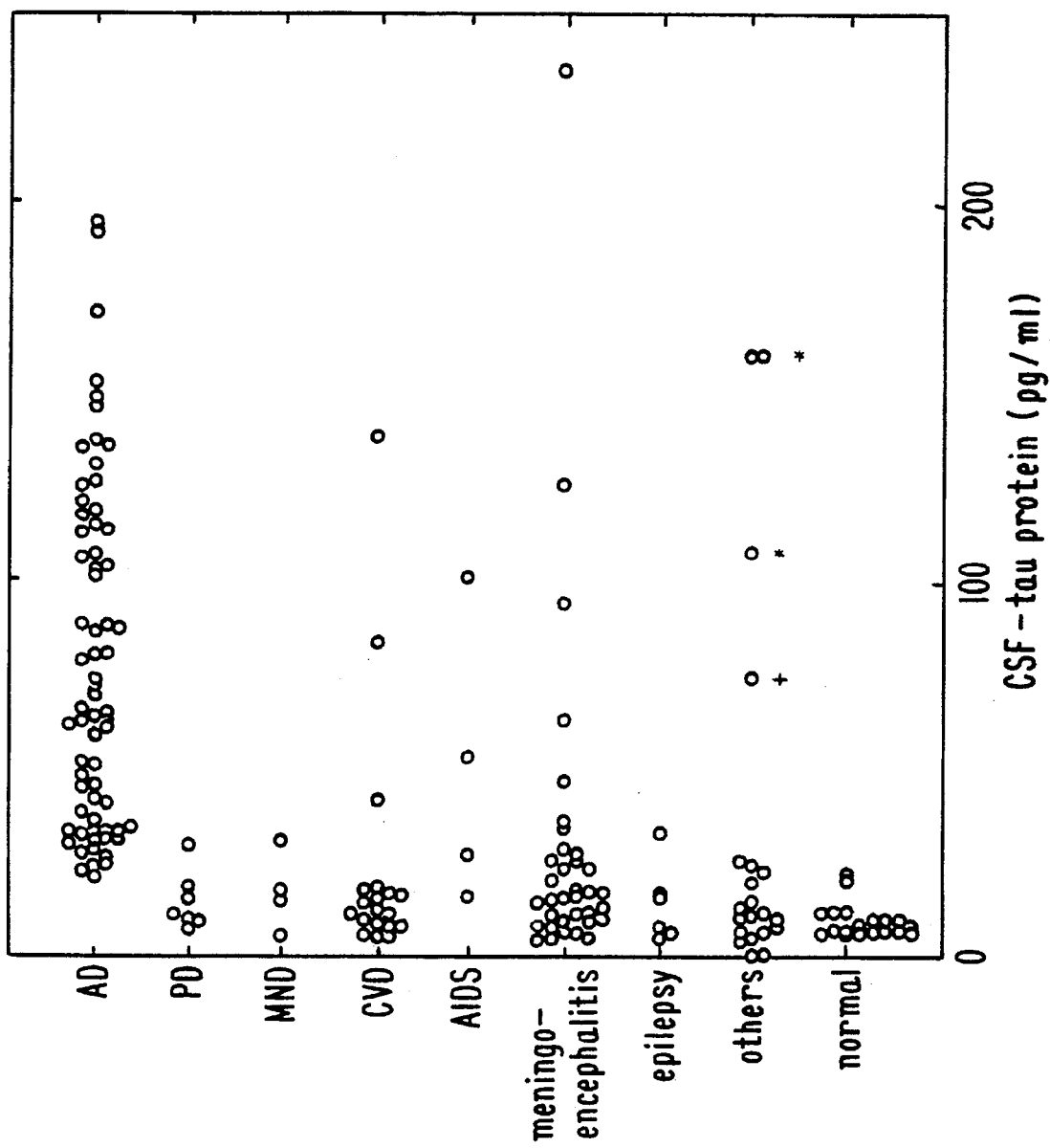

FIG. 4 shows CSF-τ levels were measured in patients with Alzheimer's Disease (AD, n=70), Parkinson's Disease (PD, n=7), motor neuron disease (MND, n=4), cerebrovascular disease (CVD, n=19), acquired immuno-deficiency syndrome (AIDS, n=4), meningoencephalitis (n=35), other neurological diseases (others, n=21) and normal controls (normal, n=19).

Figure 5:
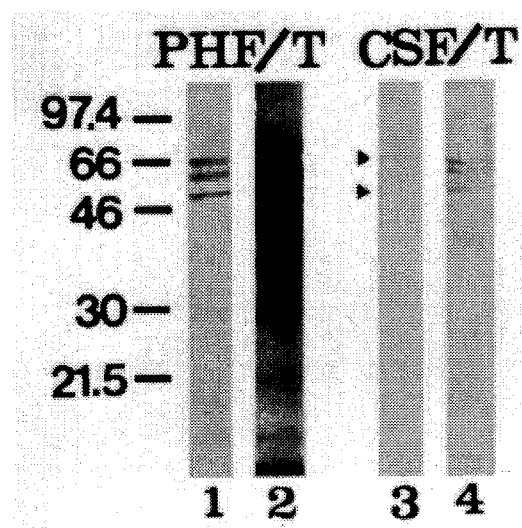

FIG. 5 shows CSF-τ was also detected by Western blotting. Purified PHF-τ was incubated with ALZ50 (1:50, lane 1) and PHF1 (1:1000, lane 2). AD-CSFs were probed with PHF-1 (lanes 3–4). The CSF-τ concentrations in lanes 3 and 4 were 194.1 and 42.5 pg/ml, respectively. Molecular mass markers are on the left (kD). The arrowheads identify the immunoreactive CSF-τ bands in lanes 3 and 4. These CSF-τ proteins displayed an electrophoretic mobility similar to PHF-τ in AD brain (lanes 1–2).

DETAILED DESCRIPTION OF THE INVENTION

As used herein, the term τ refers to the smallest isoform that is lacking alternatively spliced inserts as described in M. Goedert, M. G. Spillantini, M. C. Potier, J. Ulrich, R. A. Crowther, EMBO J. 1989, 8, 393; M. Goedert, M. G. Spillantini, R. Jakes, D. Rutherford, R. A. Crowther, Neuron 1989, 3, 519.

The peptide useful in the invention consists essentially of the sequence Lys Ser Pro Val (SEQ ID NO: 3) and can be flanked by amino acids. The peptide conveniently is in the range from 4 to about 40 amino acids in length. Although the peptide could be longer, economies govern the length of useable peptides. The flanking sequences conveniently comprise amino acids substantially corresponding to the amino acids sequences flanking Lys Ser Pro Val (SEQ ID NO: 3) in τ. The peptide as described above is abnormally phosphorylated at the serine residue in the sequence Lys Ser Pro Val (SEQ ID NO: 3). The term "abnormally phosphorylated" as used herein refers to a site on Lys Ser Pro Val (SEQ ID NO: 3), preferably the Ser, that is phosphorylated but is not occupied by a phosphate moiety in the corresponding Lys Ser Pro Val (SEQ ID NO: 3) sequence(s) in indigenous normal human τ.

Of course the peptide can be detectably labeled.

The phosphopeptides can be prepared synthetically as for example described in (16). Briefly, coupling is with commercially available Fmoc-amino acid pentafluorophenyl esters, with base used at each cycle to cleave Fmoc. Phosphorylation of the serine residue left unprotected on the peptide-resin is achieved with dibenzylphosphochloridate, and finally trifluoroacetic acid is used to remove side-chain protecting groups, and to cleave the peptide from the resin in the same step. The precursor peptide, i.e., prior to phosphorylation, can be efficiently prepared using any of numerous well known synthetic or recombinant techniques and then phosphorylated. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

The most commonly used procaryote system for the production of recombinant proteins remains E. coli, however, other microbial strains may also be used, such as Bacilli, for example Bacillus subtilis, various species of Pseudomonas, or other bacterial strains. In such procaryotic systems, plasmid vectors which contain replication sites and control sequences derived from a species compatible with the host are used. Commonly used procaryotic control sequences include promoters for transcription initiation, optionally with an operator, along with ribosome binding site sequences.

A wide variety of eucaryotic hosts are also now available for production of recombinant foreign proteins. As in bacteria, eucaryotic hosts may be transformed with expression systems which produce the desired protein directly, but more commonly, signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g., the baculovirus polyhedron promoter. As above, promoters can be either constitutive or inducible. For example, in mammalian systems, the MTII promoter can be induced by the addition of heavy metal ions.

The particulars for the construction of expression systems suitable for desired hosts are known to those in the art. For recombinant production of the protein, the DNA encoding it is suitably ligated into the expression system of choice, and the system is then transformed into the compatible host cell which is then cultured and maintained under conditions wherein expression of the foreign gene takes place. The peptide of this invention thusly produced is recovered from the culture, either by lysing the cells or from the culture medium as appropriate and known to those in the art.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art.

Antibodies specifically reactive with the abnormally phosphorylated τ peptide are also included within the scope of the invention. An antibody is said to be "specifically reactive" with a molecule if it is capable of binding with the molecule to thereby couple the molecule to the antibody. The term "epitope" is meant to refer to that portion of a hapten which can be recognized and bound by an antibody. An antigen may have one or more than one epitope. An "antigen" is capable of inducing an animal to produce antibody capable of binding to an epitope of that antigen. The specific reaction referred to above is meant to indicate that the antigen will immunoreact, in a highly selective manner, with its corresponding antibody and not with the multitude of other antibodies which may be evoked by other antigens. For example, the antibody referred to as PHF-1, immunoreacts selectively with abnormally phosphorylated τ in the CSF, referred to as CSF-τ.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab'$_2$) fragments lack the Fc fragment of intact antibody, clear more rapidly from the circulation, and may have less non-specific tissue binding of an antibody.

The antibodies of the present invention may be prepared by any of a variety of methods, for example as described in (8). Methods for the production of such antibodies are well known and described fully in the literature. See e.g., Sambrook et al., "Molecular Cloning A Laboratory Manual", second ed. Cold Spring Harbor Press, Vol. 3, Ch. 18 (1989). For example, the peptide or cells expressing the peptide, can be administered to an animal in order to induce the production of sera containing polyclonal antibodies that are capable of binding the peptide.

Monoclonal antibodies can be prepared using known hybridoma technology. In general, such procedures involve immunizing an animal with an peptide antigen. The splenocytes of such animals are extracted and fused with a suitable myeloma cell line. Any suitable myeloma cell line may be employed in accordance with the present invention. After fusion, the resulting hybridoma cells are selectively maintained in a suitable medium and then cloned by limiting dilution. The hybridoma cells obtained through such a selection are then assayed to identify clones which secrete antibodies capable of binding the peptide of the invention.

The antibodies can be detectably labeled as is known in the art.

The invention in another aspect provides a method of diagnosing a disease associated with the accumulation of paired helical filaments in a person. Such diseases include Alzheimer's Disease, Down's syndrome, etc.

The method comprises identifying in a test sample from the person, τ which has an abnormally phosphorylated serine in the sequence Lys Ser Pro Val (SEQ ID NO: 3). "Test sample" as used herein refers to any biological sample from the person that is suspected of containing τ. The test sample can comprise brain tissue having neurofibrillary tangles, such as hippocampal tissue or frontal cortex tissue or the test sample can comprise cerebrospinal fluid (CSF). In a preferred embodiment, the test sample comprises CSF and the protein identified is CSF-τ.

Identification of abnormally phosphorylated τ conveniently comprises identifying in the test sample (1) antigens capable of binding with antibodies specifically reactive with a peptide comprising the sequence Lys Ser Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated or (2) antibodies specifically reactive with a peptide comprising the sequence Lys Ser Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated.

The identification of abnormally phosphorylated τ-can conveniently be accomplished by biochemical or cytochemical means or by enzyme immunoassay such as described in ABBOTT ALZEIA (Brain), Abbott Laboratories Diagnostic Division, Abbott Park, Ill. When biochemical means are used, generally 0.5 to 1 g of tissue containing tangles is used, run on gel and identified by Western blot. Such a technique is believed to be adequate in the absence of age matched controls which have been shown to be non-reactive with the antibodies of the invention. Cytochemical means, staining, has shown some reactivity with normal tissue and could benefit by a comparison to age matched controls, whereby an increased amount of reactivity is indicative of the presence of abnormally phosphorylated τ.

Cerebrospinal fluids (CSFs) from patients with AD and patients with non-AID neurological disease as well as normal subject were surveyed by sandwich enzyme-linked immunosorbent assay (ELISA) to quantitate levels of abnormally phosphorylated τ. The CSF-τ level was significantly increased in AD patients as compared with that in patients with non-AD neurological diseases and controls. In AD, the significant increase was found irrespective of age of onset, apolipoprotein E genotype and clinical stage. Western blots of AD CSF proteins revealed two to three τ immunoreactive bands with apparent molecular weight between 50 and 65 kD consistent with phosphorylated CSF-τ. These results indicate that CSF-τ reflects that progressive accumulation of altered τ due to the progressive death of neurons in the AD brain. Thus, the assay of CSF-τ by ELISA serves as a reliable and early diagnostic test for AD.

Also provided is a test kit for diagnosing a disease associated with the accumulation of paired helical filaments comprising: (a) antigens capable of binding with antibodies specifically reactive with a peptide comprising the sequence Lys Ser Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated or (b) antibodies specifically reactive with a peptide comprising the sequence Lys Ser Pro Val (SEQ ID NO: 3) and flanked by amino acids such that said peptide is in the range from 4 to about 40 amino acids in length and characterized in having said Serine in the sequence Lys Ser Pro Val (SEQ ID NO: 3) abnormally phosphorylated.

The following examples are provided for illustrative purposes only and are not intended to limit the invention.

EXAMPLES

Example 1:

Immunological, and Morphological Studies of τ, A68, and PHFs

A68 proteins were purified from brains of patients with AD by a modification of a procedure described in (7). After sarkosyl (N-lauroyl-N-methylglycine) extraction and centrifugation, pellets containing A68 were resuspended in buffer [0.1 MMES, 0.17 M NaCl, 1 mM $MgCl_2$, 1 mM EGTA, pH 7.0], boiled for 5 minutes, and loaded onto a 1.0 to 2.5 M sucrose gradient. Highly purified A68 proteins, which were completely solubilized in SDS sample buffer, were recovered between the 2.25 to 2.5 M sucrose fractions and consisted of three to four polypeptides with an $M_r$ of 60 to 68 kD (FIG. 1A, lane 3). However, the 1.25 to 1.5 M and 1.75 to 2.0 M sucrose fractions also contained A68 that was partially soluble in SDS sample buffer, but it was contaminated with other proteins and some SDS-insoluble material excluded from gels (FIG. 1A, lanes 1 and 2, respectively). Nevertheless, this protocol allowed isolation of highly purified A68 consistently from NFT-rich cortex from patients with AD (n=9) and from elderly individuals with Down's syndrome (n=3) (8). Material from each of these sources yield results qualitatively similar to those in FIG. 1A. In contrast, A68 was not detectable in regions of AD brain (that is, cerebellum) devoid of NFTs or in cortex from age-matched controls (n=4) (8).

When the highly purified A68 preparations (as in FIG. 1A, lane 3) were placed on Formvar-coated nickel grids, negatively stained with methanolic uranyl acetate, and viewed by electron microscopy, abundant filaments approximately 10 nm in diameter were observed that were paired and twisted like classical PHFs (FIG. 1B and C). These filaments were always paired with a helical periodicity of 75 to 80 nm. In paired arrays, these filaments with diameters of 10 nm exhibited diameters of 20 nm at the constrictions; the maximum diameter was 30 to 40 nm. Thus, they were indistinguishable from AD PHFs in situ (1). These biochemical and electron microscopic data indicate that PHFs are composed of A68 and that no other proteins are required for the formation of PHFs from the A68 proteins prepared as described here.

Example 2:

Amino Acid Composition and Sequencing Analyses of A68 Preparations

The composition of all A68 isoforms revealed a large number of Pro, Lys, and Gly residues (9), which is characteristic of human τ (10). However, because the complete amino acid sequence of each human τ isoform is still unknown, the smallest A68 isoform was compared with the smallest τ isoform (that is, τ lacking alternatively spliced inserts) (10). These two forms had similar amino acid compositions (9). The NH$_2$-terminus of A68 could not be sequenced because it was blocked. However, three fragments with M$_r$ of 18, 21, and 23 kD were recovered from cyanogen bromide digests of A68, and each was sequenced. The first 14 amino acids of the 18-kD fragment [that is, Pro Asp Leu Lys Asn Val Lys Ser Lys Ile Gly Ser Thr Glu (SEQ ID NO: 1)] were identical to residues 251 to 264 of normal human τ [numbering system as in (10)]. Identical sequences from the 18-kD fragments were obtained with an A68 preparation from a single AD brain and from pooled gray matter dissected from five different AD brains. The 21-kD fragment was sequenced through 14 cycles, and this sequence was identical to residues 128 to 141 of human τ [that is, Val Ser Lys Ser Lys Asp Gly Thr Gly Ser Asp Asp Lys Lys (SEQ ID NO: 2)]. However, the recovery of Ser$^{137}$ was unusually low, suggesting that it may be phosphorylated. Finally, the 23-kD fragment included sequences from both the 18- and 21-kD fragments, suggesting incomplete cyanogen bromide digestion. Because the sequences derived from these fragments corresponded to regions in τ separated by more than 100 residues, it is likely that A68 contains the entire τ molecule.

Example 3:

Comparisons of the Properties of A68 and τ

Figure 2F:
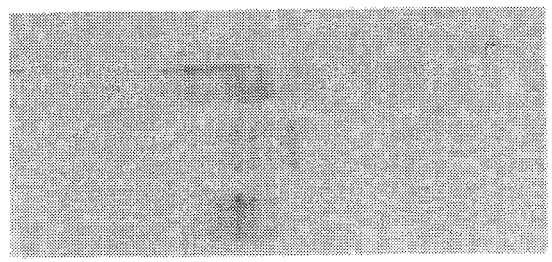
Figure 2E:
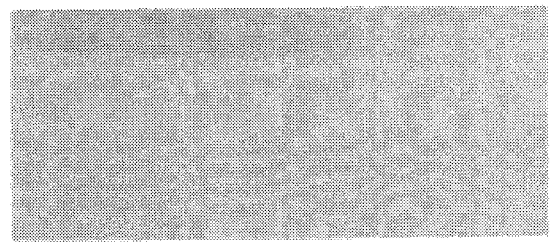
Figure 2D:
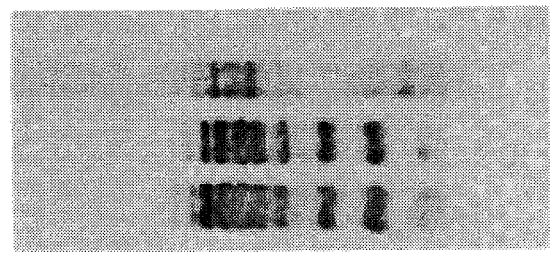
Figure 2C:
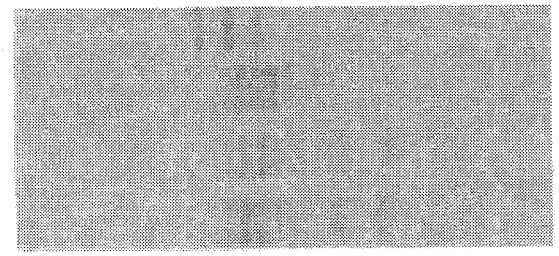
Figure 2B:
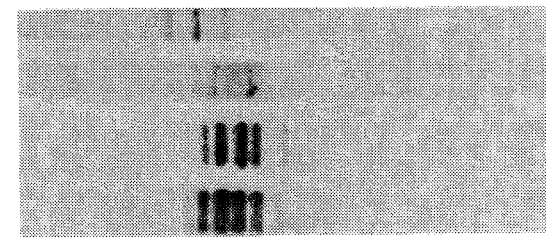
Figure 3A:
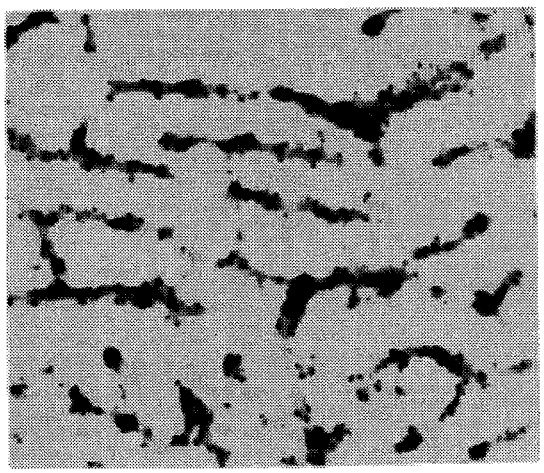
Figure 3B:
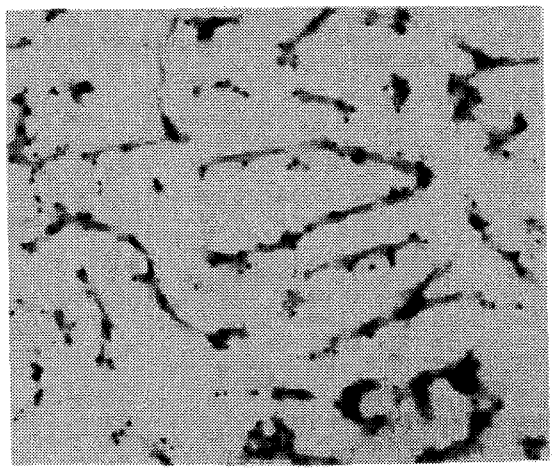
Figure 3C:
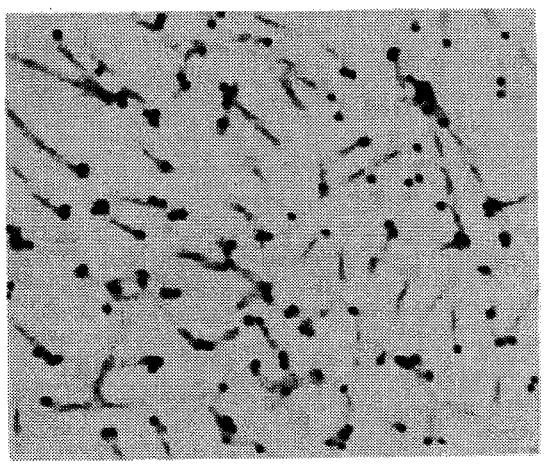
Figure 3D:
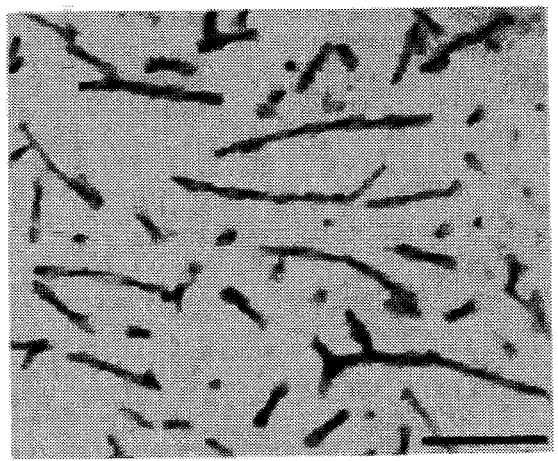

Comparisons of the properties of A68 and τ were extended to include immunoblot and immuno-electron microscopic studies using seven MAbs specific for identified epitopes distributed along the entire length of τ (5–7, 12, 13). All of these MAbs to τ, including T46 (which binds to the COOH-terminus of τ) and ALZ50, recognized all A68 isoforms in immunoblots except for the Tau-1 MAb (FIG. 2B, C, and D). However, Tau-1 did recognized dephosphorylated A68 (lane 3, FIG. 2D) as noted earlier (7, 13, 14). In the immuno-electron microscopic studies, PHFs from purified A68 fractions reacted with the same group of MAbs to τ in addition to ALZ50. This is significant because the epitopes recognized by these MAbs extend over almost the entire length of τ (13), and none of these τ epitopes are absent from A68-derived PHFs. Immunodecoration patterns of the A68-derived PHFs were obtained with the MAbs T14 (which binds an epitope in the NH$_2$-terminal third of τ) (FIG. 3A) and T46 (which binds the COOH-terminus of τ) (FIG. 3B). In contrast, antibodies to other putative PHF components (NF), β-amyloid proteins never recognized A68 either in protein immunoblots or as PHFs on grids (9). These data provide further evidence that pHFs are composed of A68 and that A68 is derived from τ.

Example 4:

Distinguishing τ from A68

To distinguish τ from A68, antisera to a motif in τ was developed, that is, the single Lys Ser Pro Val (SEQ ID NO: 3) at residues 395 to 398 (10). This Lys Ser Pro Val (SEQ ID NO: 3) sequence was focused on because Lys Ser Pro Val-specific MAbs recognized all τ isoforms without enzymatic dephosphorylation in protein immunoblots, but they only reacted with AD NFTs in tissue sections after enzymatic dephosphorylation (15). The Lys Ser Pro Val (SEQ ID NO: 3) sequence in τ is believed to be an abnormal phosphate acceptor site; therefore, the transformation of τ into A68 might involve the abnormal phosphorylation of Ser$^{396}$. To test this possibility, the peptide (the T3 peptide) based on residues 389 to 402 [Gly Ala Glu Ile Val Tyr Lys Ser Pro Val Val Ser Gly Asp (SEQ ID NO: 4)] in human τ was synthesized. A phosphorylated form of this T3P peptide also was prepared by selective phosphorylation of the first Ser (that is, Ser$^{396}$ in human π) as described (16). Antisera were prepared to each peptide (8), and the specificity of these two antibodies for τ and A68 was assessed in immunoblots. The antiserum to T3P recognized A68 but not normal human τ, and the antibody to T3 recognized τ but not A68 (FIG. 2E and F). This result implies that a phosphate at Ser$^{396}$ distinguishes A68 from normal human τ, that Ser$^{396}$ in the τ Lys Ser Pro Val (SEQ ID NO: 3) motif is not a normal phosphate acceptor site in τ, and that the conversion of normal human τ to A68 could be in part due to the phosphorylation of Ser$^{396}$. To test the ability of these two antisera to bind other neuronal cytoskeletal proteins with Lys Ser Pro Val (SEQ ID NO: 3) motifs, that is, NF proteins (15), protein immunoblots of brain homogenates enriched in these proteins were probed with both antisera and it was found that no other proteins reacted with these antibodies. Thus, unique sequences flanking the Lys Ser Pro Val (SEQ ID NO: 3) motif of τ, A68, and the two peptides described here are believed to specify two distinct conformations that are differentially recognized by the antibodies to T3 and to T3P.

Example 5:

Antibodies Binding to PHFs Derived from Purified A68 and in situ NFTs

Figure 3E:
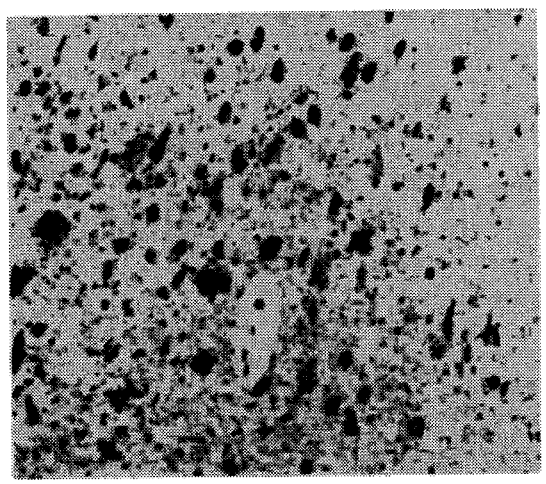
Figure 3F:
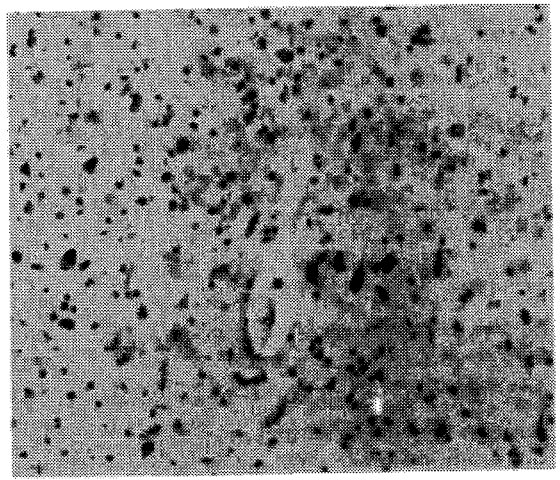

The antiserum to T3P (FIG. 3C), but not the antibody to T3 (FIG. 3D), decorated isolated A68-derived PHFs, suggesting that these PHFs contain A68 but not normal τ. When sections (frontal cortex, hippocampus) of AD (n=5) and Down's syndrome (n=2) brains rich in lesions composed of PHFs (that is, NFTs, SPs, and NTs) were probed with these same two antisera using the immunoperoxidase method (8, 12, 15), the antibody to T3P stained abundant NFTs, SP coronas, and NTs (FIG. 3E). By contrast, the antibody to T3 failed to stain SP coronas and NTs, but it did stain a few NFts, especially in cases with very large numbers of NFTs (FIG. 3F). This may reflect a redistribution of normal τ from the axons to the perikarya of neurons as risk for NFT formation in AD (1, 8 17). Only the antibody to T3P consistently stained the occasional hippocampal NFTs in age-matched controls (n=3), (9). Thus, these observations are consistent with the notion that A68 is present in most, if not all types of pathology associated with the accumulation of PHFs (that is, NFTs, Sp neurites, and NTs).

Example 6:

Inappropriate Phosphorylation in the Transformation of τ to A68

Preparations of both τ and A68 were dephosphorylated with *Escherichia coli* alkaline phosphatase (15). The enzymatic dephosphorylation of normal τ resulted in a slight increase in the electrophoretic mobility of most τ isoforms.

Figure 2A:
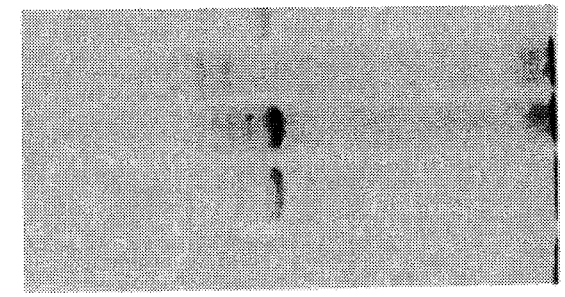

In contrast, all A68 isoforms showed a significant drop in $M_r$ after the same treatment (FIG. 2A). The dephosphorylated A68 proteins all migrated to positions in the gel very close to those of dephosphorylated τ (FIG. 2A). More importantly, A68 was detectable by the antibodies to both Tau-1 and T3 after enzymatic dephosphorylation (FIG. 2D and F), and dephosphorylation abolished the immunoreactivity of A68 with the antiserum to T3 P (FIG. 2E). These data confirmed that two sites, that is, the Lys Ser Pro Val (SEQ ID NO: 3) motif and the Tau-1 epitope, are phosphorylated in A68 but not in normal τ. Finally, since the dephosphorylation of A68 proteins reduced their $M_r$, such that the gel migration pattern of these polypeptides was similar to that of dephosphorylated τ, it was inferred that the abnormal phosphorylation of endogenous normal τ plays a major role in the conversion of τ to A68.

Example 7:

Patient Population

Sixty-nine patients with probable AD and 1 patient with autopsy confirmed AD (73.9 ±8.9 years, early-onset AD/late-onset AD: 22/48), 7 patients with Parkinson's Disease (PD, 70.6 ±3.8 years), 4 patients with motor neuron disease (MND, 66.0 ±12.9 years), 19 patients with cerebrovascular disease (CVD, 67.1 ±12.9 years), 4 patients with acquired immuno-deficiency syndrome (AIDS, 38.0±4.7 years) 35 patients with meningoencephalitis (33.9±14.8 years), 6 patients with epilepsy (48.3±23.0 years), 21 patients with other neurological diseases (58.3±14.8 years), and 19 normal subjects without the presence of any confirmed neuropsychiatric disease (44.3±18.5 years) were studied. Patients with other neurological diseases included those with myopathy (n=4), Creutzfeldt-Jacob disease (CJD, n=3), progressive supranuclear palsy (PSP, n=3), normal pressure hydrocephalus (NPH, n=3), multiple sclerosis (n=3), cerebillitis (n=1), neurosyphilis (n=1), chronic inflammatory demyelinating polyradiculoneuropathy (n=1), Bell's palsy (n=1) and transverse myelitis (n=1). The clinical diagnosis of probable AD was established by NINCDS-ADRDA criteria (21) and the neuropathological diagnosis was confirmed according to the criteria recommended by National Institute of Aging (22).

Example 8:

CSF Collection, Quantitative τ Assay and Immunoblot Analysis

CSF was collected by routine lumbar puncture and centrifuged at 1500 rpm for 10 minutes. The samples were then aliquoted and stored at −80° C. until analysis. CSF-τ levels were determined using a sensitive enzyme-linked immunosorbent assay (Innogenetics, Belgium) in accordance with the manufacturer's instructions. The assays of CSF-τ were performed in duplicate, and the variation between samples in the duplicate assays was <10%. In a subset of patients τ was assayed in serum that was obtained at the same time the spinal tap was performed. Statistical analysis was performed using Student's t-test. To characterize CSF-τ proteins, 50 μl of CSF from AD and non-AD patients were freeze-dried and then subjected to 10% SDS-PAGE and Western blot. PHF/τ was purified from the temporal cortex of a 77 year old man who was pathologically confirmed to have AD. Epitope specific anti-τ mouse monoclonal antibodies, PHF-1, ALZ50, τ-14 and τ-1, were used in these studies. The protein concentration in the CSF samples was determined using bichinchoninic acid as a dye reagent with bovine serum albumin as a standard.

In the 19 normal subjects, the CSF-τ level was 9.0±4.5 pg/ml (Mean±S.D.) and it gradually increased with age. In the normal controls, CSF-τ constituted approximately $2 \times 10^{-6}\%$ of total CSF proteins. In contrast, the CSF-τ levels were significantly increased (P<0.001) in the AD patients (76.9±45.4 pg/ml) compared with those with non-AD neurological diseases (27.8±38.7 pg/ml) and normal controls. There was only a small overlap between the values for the AD and non-AD subjects although extremely high CSF-τ levels in some patients with CVD, AIDS, meningoencephalitis, CJD and NPH (FIG. 4). No τ proteins were detected in serum.

The CSF-τ levels in AD patients with early (<65 years of age) or late (>65 years of age) onset of their disease were 77.7±45.9 pg/ml and 76.6±45.6 pg/ml, respectively, and the CSF-τ levels were not significantly different in AD patients with different Apo E alleles: 3/3 (72.6±38.4 pg/ml), 4/3 (81±49.5 pg/ml) and 4/4 (63.0±40.2 pg/ml). Furthermore, CSF-τ levels were not significantly different as AD progressed.

The specificity of the CSF-τ assay by ELISA was verified by probing CSF proteins with a panel of anti-τ antibodies. As shown in FIG. 5, two or three immunobands with an apparent molecular weight ranging between 50 and 65 kD were detected with the PHF-1 monoclonal antibody in the CSF of AD patients. However, these immunobands were not detectable with any of the other anti τ antibodies used, i.e., ALZ50, τ-14 and τ-1. For Western blotting, neither boiling CSF at 95° C. for 10 minutes or pretreatment of CSF with 2.5% perchloric acid enhanced detection of CSF-τ.

CONCLUSIONS

Two major conclusions emerge from the data presented herein: (i) A68 proteins are major subunits of an SDS-soluble form of PHFs and (ii) A68 contains amino acid sequences identical to those in spatially separate regions of normal human τ. This establishes that A68 is derived from τ itself and that regions extending from the $NH_2$ to the COOH-terminal domains of τ are present in PHFs, albeit in a modified form.

The data also suggest that abnormal phosphorylation plays a major mechanistic role in the sequence of events leading to the formation of PHFs from normal τ, and one potential abnormal phosphate acceptor site was identified as $Ser^{396}$ in the normal human τ Lys Ser Pro Val (SEQ ID NO: 3) motif. It is significant that this Lys Ser Pro Val (SEQ ID NO: 3) motif is present in all τ isoforms and is located near the microtubule binding repeats (residues 244 to 368) (10, 18). The phosphorylation of $Ser^{396}$ may account for the inability of A68 to bind to microtubules, and this may result form a change in the secondary structure of the residues contained within the T3 peptide as measured by circular dichroism (9). However, the aberrant phosphorylation of other Ser residues also could play a role in the transformation of τ into A68. Two candidates are the Ser residues in the Tau-1 epitope (within amino acid 189 to 207 of τ) (13), and in the recently identified Lys Glu Ser Pro (SEQ ID NO: 5) motif (amino acid 44 to 47 of τ) (19).

REFERENCES

1. H. C. Chui, Arch. Neurol. (Chicago) 46, 806 (1989), D. L. Price et al., BioEssays 10, 69 (1989); D. J. Selkoe, Annu. Rev. Neurosci, 12, 463, (1989); J. Q. Trojanowski et al, Annu. Rev. Gerontol. Ceriat., 10, 167 (1991); C. M. Wischik, Curr. Opin. Cell Biol. 1, 115 (1989)

2. S. G. Greenberg and P. Davies, Proc. Natl. Acad. Sci. U.S.A. 87, 5827 (1990)
3. M. Geodert et al., ibid, 85, 4051 (1988); J. Kondo et al., Neuron 1, 827 (1988), C. M. Wischik et al, Proc. Natl. Acad. Sci. U.S.A. 85, 4506,(1988)
4. B. L. Wolozin et al., Science 232, 648 (1986); B. L. Wolozin et al. Proc. Natl. Acad. Sci. U.S.A. 85, 6202 (1988)
5. H. Ksiezak-Reding et al., J. Biol. Chem. 263, 7943 (1988); N. Nukina et al., Neurosci. Lett. 87, 240 (1988).
6. H. Ksiezak-Reding et al., J. Neurosci, Res. 25, 420 (1990)
7. H. Ksiezak-Reding et al., J Neurosci Res 25:412 (1990)
8. H. Arai, et al., Proc. Natl. Acad. Sci. U.S.A. 87, 2249 (1990); M. L. Schmidt. V. M.-Y. Lee J. Q. Trojanowski, Am. J. Pathol. 136, 1069 (1990); R. A. Stern, L. Otvos. Jr., J. Q. Trojanowski, V. M.-Y. Lee, ibid, 134, 973 (1989)
9. V. M.-Y. Lee, B. J. Balin, L. Otvos. Jr., J. Q. Trojanowski, unpublished data
10. M. Goedert, M. G. Spillantini, M. C. Potier, J. Ulrich, R. A. Crowther, EMBO J. 8, 393 (1989); M. Goedert, M. G. Spillantini, R. Jakes, D. Rutherford, R. A. Crowther, Neuron 3 519 (1989)
11. R. B. Vallee, J. Cell Biol. 92, 435 (1982) 12. J. Q. Trojanowski, T. Schuck, M. L. Schmidt, V. M. Y-Lee, J. Histochem. Cytochem. 37, 209 (1989)
13. K. S. Kosik et al., Neuron 1, 816 (1988)
14. Grundke-Iqbal et al., Proc. Natl. Acad. Sci. U.S.A. 83, 4913 (1986)
15. V. M.-Y. Lee et al., ibid, 85, 1998 (1988); V. M.-Y. Lee, L. Otvos, Jr., M. L. Schmidt, J. Q. Trojanowski, ibid, p. 7384.
16. L. Otvos et al., Int. J. Pept. Protein Res. 34, 129 (1989)
17. Y. Ihara, Brain Res. 459, 138 (1988); N. W. Kowall and K. S. Kosik. Ann. Neurol. 22, 639 (1987); A. C. McKee et al., ibid. 26, 652 (1989)
18. D. W. Cleveland, Cell. 60, 701 (1990), G. Lee et al., Neuron 2, 1615 (1989); S. A. Lewis et al., Nature 342, 498 (989)
19. K. Iqbal et al. , Proc. Natl. Acad. Sci. U.S.A. 86, 5646(1989)
20. T Miyakawa et al., Virchows Arch. B 57, 267 (1989)
21. G. McKhann et al., Neurology 34, 939 (1984)
22. Z. S. Khachaturian, Arch. Neurol. 42, 1097 (1985)

What is claimed is:

1. A method of detecting abnormally phosphorylated τ in a test sample, said method comprising:
   (a) contacting a test sample with an antibody which specifically reacts with τ which has an abnormally phosphorylated serine in the sequence LysSerProVal (SEQ ID NO:3); and,
   (b) detecting the presence of said antibody bound to said τ.

2. The method of claim 1 wherein the test sample comprises cerebrospinal fluid.

3. The method of claim 1 wherein said antibody is a monoclonal antibody.

4. The method of claim 1 wherein said antibody is detectably labeled.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 14
        ( B ) TYPE: Amino Acid
        ( D ) TOPOLOGY: Linear ( x i ) SEQUENCE DESCRIPTION: SEQ ID NO: 1:

```
Pro  Asp  Leu  Lys  Asn  Val  Lys  Ser  Lys  Ile  Gly  Ser  Thr  Glu
1                  5                          10
```

( 2 ) INFORMATION FOR SEQ ID NO: 2:

( i ) SEQUENCE CHARACTERISTICS:
        ( A ) LENGTH: 14
        ( B ) TYPE: Amino Acid
        ( D ) TOPOLOGY: Linear ( x i ) SEQUENCE DESCRIPTION: SEQ ID NO: 2:

```
Val  Ser  Lys  Ser  Lys  Asp  Gly  Thr  Gly  Ser  Asp  Asp  Lys  Lys
1                  5                          10
```

( 2 ) INFORMATION FOR SEQ ID NO: 3:

( i ) SEQUENCE CHARACTERISTICS:
        ( A ) LENGTH: 4
        ( B ) TYPE: Amino Acid
        ( D ) TOPOLOGY: Linear ( x i ) SEQUENCE DESCRIPTION: SEQ ID NO: 3:

```
Lys  Ser  Pro  Val
1
```

( 2 ) INFORMATION FOR SEQ ID NO: 4:

( i ) SEQUENCE CHARACTERISTICS:
        ( A ) LENGTH: 14
        ( B ) TYPE: Amino Acid (D) TOPOLOGY: Linear (x i) SEQUENCE DESCRIPTION: SEQ ID NO: 4:

Gly Ala Glu Ile Val Tyr Lys Ser Pro Val Val Ser Gly Asp
1               5                   10

(2) INFORMATION FOR SEQ ID NO: 5:

(i) SEQUENCE CHARACTERISTICS:
      (A) LENGTH: 4
      (B) TYPE: Amino Acid
      (D) TOPOLOGY: Linear (x i) SEQUENCE DESCRIPTION: SEQ ID NO: 5:

Lys Glu Ser Pro
1